(12) United States Patent
Hauger

(10) Patent No.: US 9,603,433 B2
(45) Date of Patent: Mar. 28, 2017

(54) INTERNALLY SUPPLIED APPLICATOR WITH FINGERS AND FOIL PACKET

(71) Applicant: GEKA GmbH, Bechhofen (DE)

(72) Inventor: Christian Hauger, Donaueschingen (DE)

(73) Assignee: GEKA GmbH, Bechhofen (DE)

( * ) Notice: Subject to any disclaimer, the term of this patent is extended or adjusted under 35 U.S.C. 154(b) by 84 days.

(21) Appl. No.: 14/678,373

(22) Filed: Apr. 3, 2015

(65) Prior Publication Data

US 2015/0282589 A1  Oct. 8, 2015

(30) Foreign Application Priority Data

Apr. 3, 2014 (DE) ..................... 20 2014 002 986 U

(51) Int. Cl.
| | |
|---|---|
| *B43K 5/14* | (2006.01) |
| *A45D 34/04* | (2006.01) |
| *A46B 11/00* | (2006.01) |
| *A45D 24/26* | (2006.01) |
| *A61M 35/00* | (2006.01) |
| *B65D 75/36* | (2006.01) |
| *B65D 77/20* | (2006.01) |

(52) U.S. Cl.
CPC ........... *A45D 34/042* (2013.01); *A45D 24/26* (2013.01); *A46B 11/0075* (2013.01); *A61M 35/003* (2013.01); *B65D 75/366* (2013.01); *B65D 77/2024* (2013.01); *A61M 2207/00* (2013.01)

(58) Field of Classification Search
CPC  A61M 35/003; A61M 35/006; A46B 11/0075
USPC ................................................. 401/132–134
See application file for complete search history.

(56) References Cited

U.S. PATENT DOCUMENTS

| | | | | |
|---|---|---|---|---|
| 5,111,932 A | * | 5/1992 | Campbell | .......... B65D 75/5855 206/216 |
| 6,302,607 B1 | | 10/2001 | Burrowes et al. | |
| 8,262,608 B2 | * | 9/2012 | Clark | ................ A61B 17/00491 604/91 |
| 9,498,045 B2 | * | 11/2016 | Hartstock-Martin | A46B 11/0003 |
| 2011/0174835 A1 | | 7/2011 | Mamiye | |

FOREIGN PATENT DOCUMENTS

| | | |
|---|---|---|
| DE | 3931111 A1 | 3/1991 |
| DE | 9419660.5 U1 | 2/1995 |

(Continued)

OTHER PUBLICATIONS

Search Report from the German Patent & Trademark Office for DE 20 2014 002 986.5 dated Nov. 21, 2014.

*Primary Examiner* — Jennifer C Chiang

(57) ABSTRACT

An internally supplied applicator for applying a fluid substance, in particular a cosmetic or pharmaceutical product, having a solid finger support with preferably injection molded fingers and at least one supply conduit for conveying the substance from the side of the finger support oriented away from the fingers to the side of the finger support that is equipped with the fingers; the side of the finger support oriented away from the fingers is adjoined by a (crushable) foil packet that contains a reservoir of the substance that is to be applied so that pressing on the foil packet causes a volume of the substance, which is to be applied, to be dispensed through the supply conduit.

21 Claims, 9 Drawing Sheets

(56) References Cited

FOREIGN PATENT DOCUMENTS

| | | |
|---|---|---|
| DE | 102004014342 A1 | 9/2004 |
| DE | 60219520 T2 | 12/2007 |
| DE | 202010007365 U1 | 12/2010 |
| WO | 2004082424 A1 | 9/2004 |
| WO | 2013156648 A1 | 10/2013 |

\* cited by examiner

INTERNALLY SUPPLIED APPLICATOR WITH FINGERS AND FOIL PACKET

This application claims priority to DE 20 2014 002 986.5 filed Apr. 3, 2014, which is herein incorporated by reference in its entirety.

FIELD OF THE INVENTION

The invention relates to an internally supplied applicator for applying a fluid substance, in particular a cosmetic or pharmaceutical product, and a method for producing such an applicator.

BACKGROUND OF THE INVENTION

Applicators for applying a cosmetic or a pharmaceutical liquid with a bottle forming a reservoir and a cap carrying bristles so that the bottle itself is a part of the applicator are known in the state of the art.

Therefore it is an object of the invention to create a more economical reservoir for cosmetics or pharmaceuticals that does not only contain the cosmetics or pharmaceutical but that can be used itself as an applicator.

SUMMARY OF THE INVENTION

An internally supplied applicator for applying a fluid substance, in particular a cosmetic or pharmaceutical product, is proposed. The applicator has a solid finger support with preferably injection molded fingers and at least one supply conduit for conveying the substance from a side of the finger support oriented away from the fingers to a side of the finger support that is equipped with the fingers. The side of the finger support, oriented away from the fingers is adjoined by a crushable foil packet that contains a reservoir of the substance that is to be applied so that pressing on the foil packet causes a volume of the substance, which is to be applied, to be dispensed through the supply conduit. The finger support may be intrinsically rigid. The foil pack may be welded only to a circumference surface of the finger support. The foil packet may be a tubular foil that is extruded or blown so that it is seamless around its outer circumference direction and preferably has a wall thickness of at most 0.5 min or better still, at most 0.25 mm. The tubular foil may be intrinsically welded at its end oriented away from the finger support. The finger support may be composed of a finger-supporting plate, which on its side oriented away from the fingers, transitions integrally into a tubular fining that the foil packet and in particular the tubular foil encompasses like a stocking. The foil packet or the tubular foil may be welded to the outer circumference of the tubular fitting. The tubular fitting may taper toward its end oriented away from the finger support, and is preferably embodied in a conical shape. The finger support or its tubular fitting may transition into at least two or better still, at least four, spreading arms. The foil packet or the tubular foil may be welded to the outer circumference of the finger-supporting plate. The bristle support may be embodied in the shape of a boat. The finger support may have a thread for screwing on a screw cap or a snap element for snapping on a cap. The tubular foil may also encompass the finger support at its finger end and preferably is intrinsically welded to its end there.

According to one embodiment, an applicator unit composed of at least one applicator includes the applicator inserted into a blister pack, which is composed of a tray that has a recess that accommodates the applicator and at least the recess that accommodates the applicator, or better still, the entire tray, is sealed on one side with a foil.

According to another embodiment, an internally supplied applicator for applying a fluid substance, in particular a cosmetic or pharmaceutical product, has a static finger support with fingers injection molded onto it and at least one supply conduit for conveying the substance from the side of the finger support oriented away from the fingers to the side of the finger support that is equipped with the fingers. The side of the finger support oriented away from the fingers is adjoined by a crushable blister pack, which is composed of a tray and a foil that seals it, and which contains a reservoir of the substance that is to be applied. The attachment is embodied so that pressing on the tray and/or the foil that seals the tray causes a volume of the substance, which is to be applied, to be dispensed through the supply conduit. The tray and preferably also the foil that seals the tray is/are welded to the finger support. The finger support divides the tray into a dry region and a wet region, and the dry region accommodates the set of fingers of the finger support. The tray may be embodied so that in the dry region it has a predetermined breaking point, which makes it possible, before use, to break off the part of the tray that protects the set of fingers until the use, and to completely remove it or more it out of the way so that the application can be carried out with the aid of the set of fingers. In certain embodiments, the tray may be embodied so that in the dry region, it is sufficiently thin-walled so that it can be laterally folded over there so that the application can be carried out with the aid of the set of fingers.

A method for producing an applicator includes as tubular foil that is blown and/or extruded or produced by means of welding, and a finger support that is equipped with the fingers as described above and the finger support is at least partially slid into the tubular foil and then welded to it, after which the tubular foil is filled with the substance to be applied and then welded completely closed. The finger support may be inserted into the beginning of the tubular foil and welded to it even before the entire length of the tubular foil that is required for this applicator is blown and/or extruded. The substance to be applied may be dispensed into the tubular foil while the latter is still hot, preferably at a temperature of at least 60°.

Other functions, advantages, and embodiment possibilities of the invention ensue from the following embodiments described below with reference to the Figures.

BRIEF DESCRIPTION OF THE DRAWINGS

FIG. 8.1 shows a plan view of a modification of the exemplary embodiment illustrated in FIGS. 7 and 8.

DETAILED DESCRIPTION OF THE PREFERRED EMBODIMENTS

Figure 1:
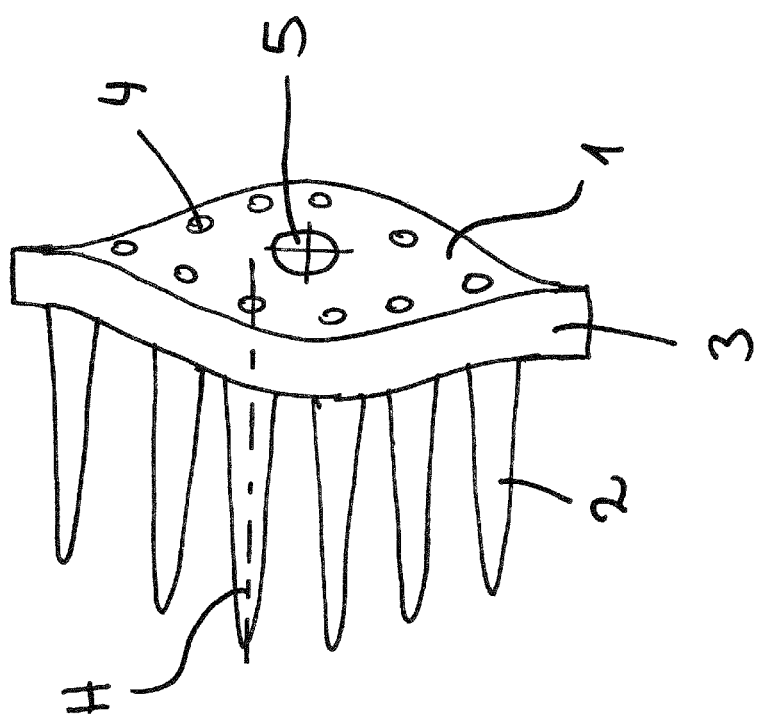
FIG. 1 shows a perspective view of the first exemplary embodiment.

FIG. 1 shows a finger support 1, which belongs to a first exemplary embodiment. In this case, the finger support is embodied in the form of a plate (finger-supporting plate), which preferably extends in an at least essentially—and ideally, completely—perpendicular fashion relative to the subsequent longitudinal axis L of the applicator.

This finger-supporting plate has an outer circumference 3, which is preferably smooth-surfaced and for example at least 0.5 cm, or better still, at least 0.75 cm thick in the direction parallel to the longitudinal axis L. This outer circumference 3 is used for welding the foil packet into place, which is not shown in detail in FIG. 1.

The finger support can have a central supply conduit 5, which is used to convey a substance that is to be applied from the side that is oriented toward the viewer in FIG. 1 to the other side that is equipped with the bristles 2 in order to make it available there for application. In addition or instead of this, at least one bristle can be hollow on the inside and can thus have a bristle conduit 4 that serves the same function.

It is particularly preferable if the finger support is boat-shaped in the direction perpendicular to the longitudinal axis L, as shown in FIG. 1. A "boat-shaped" embodiment is understood to be an embodiment that tapers to a point in at least 2 places and in the region of the points, is preferably no more than 2 mm thick or better still, is not significantly thicker than one layer of the foil 21 that forms the foil packet. The expression "not significantly thicker" here is understood to mean at most 30% or better still, at most 20%, thicker. In this way, it is particularly easy to weld the foil to the finger support.

The finger support shown in FIG. 1 can also have an integral tubular fitting; this is not graphically depicted here in FIG. 1, though, and will be illustrated in greater detail below in connection with other exemplary embodiments. In this case, the foil that forms the foil packet can also be welded to the tubular fitting instead of directly to the outer circumference of the finger-supporting plate.

In order to embody the most inexpensive possible applicator, the finger support shown in FIG. 1 is inserted into a foil packet that is preferably embodied in the form of a tubular foil 6 that is extruded or blown so that it is seamless in the circumference direction and ideally has a wall thickness of at most 0.5 mm or better still, at most 0.25 mm. Local thickened regions of the kind that are produced, for example, by a weld of two foils to each other, however, are irrelevant to these thickness specifications.

Figure 2:
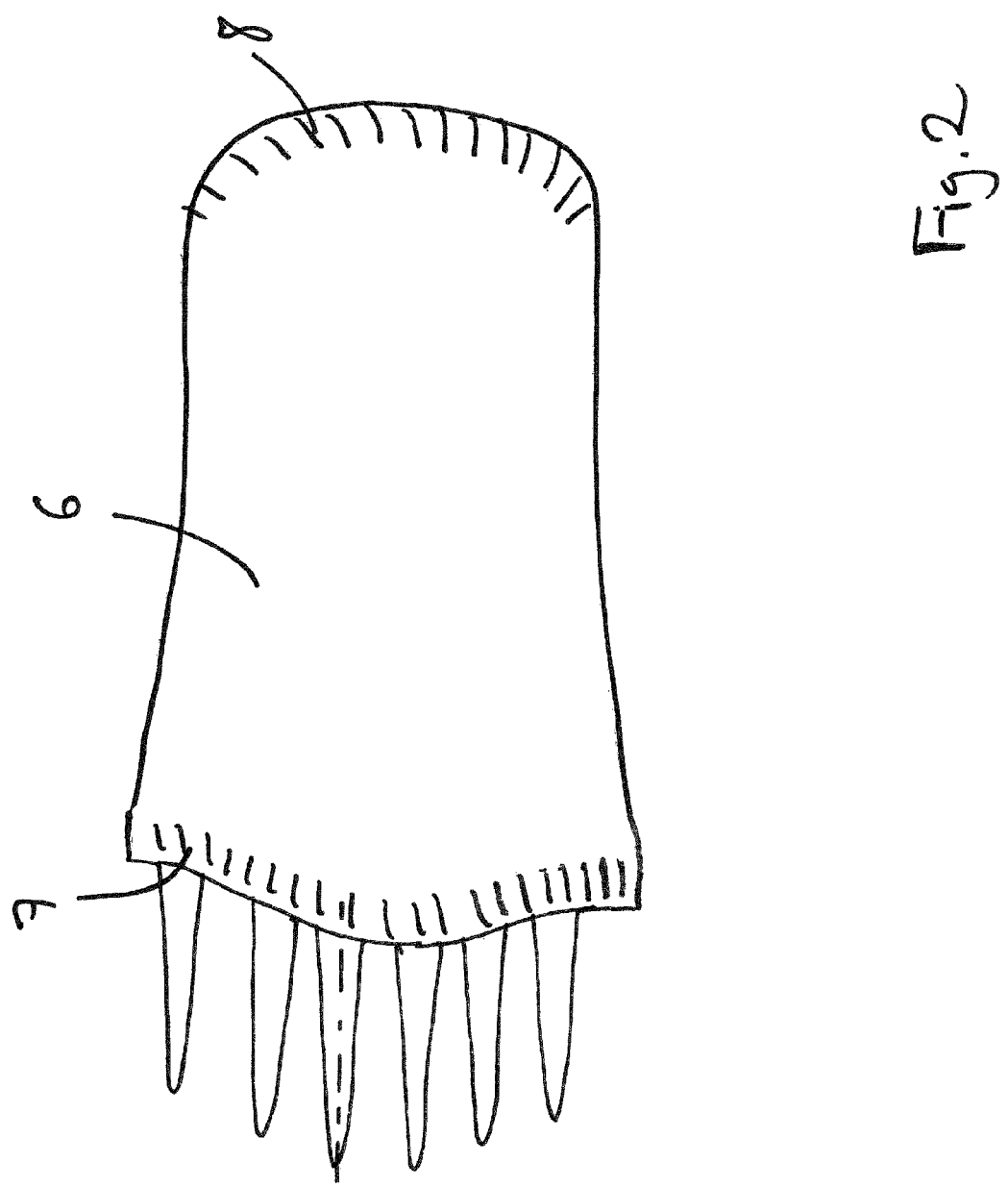
FIG. 2 shows a frontal view along of the first exemplary embodiment in its complete form.

FIG. 2 is a very clear depiction of the whole when complete. The drawing shows the welding seam 7 with which the foil packet is welded directly to the outer circumference 3 of the finger support shown in FIG. 1. The tubular foil is initially open at the end oriented away from the finger support and is filled from this end. After the tubular foil has been filled, it is pressed together and welded at the end oriented away from the finger-supporting plate; this produces the welding seam 8 shown in FIG. 2.

With regard to the finger supports described here, it should in general be noted that essentially, they are intrinsically rigid. As a result, unlike the foil that forms the foil packet, the finger support is not crushable, but instead—apart from its bristles—experiences deformations in the range below 5/10 mm, at least in response to the forces that occur during application. This definition applies to all of the finger supports described here.

With regard to the foil packet, it should also be noted that due to the low thickness of the foil, it is usually distinguished by the fact that it is crushable, i.e. the user can squeeze the foil packet so that the foil packet collapses with an indefinite number of folds.

With regard to the finger support, it should also be noted that in the context of the invention, fingers are preferably understood to mean bristles. Bristles are rod-like application elements whose length is at least 5 times greater than their maximum diameter above the rounding with which they may transition into the bristle support. Typically, bristles of this kind, are flexible so that they can be deflected laterally by an amount of at least six times the maximum bristle diameter in a direction perpendicular to the longitudinal axis of the bristle H in the unstressed state, without suffering a plastic deformation. This description of the finger support applies to all of the exemplary embodiments. The injection-molded bristles that are preferably used have a certain physical feature that differentiates them from other bristles so that the production is reflected in the physical features that are to be found in a bristle. In the injection molding of bristles, the molecular chains of the plastic that forms the bristles are aligned in a largely parallel fashion in the narrow conduits that mold the bristles, which gives a bristle the corresponding structure and significantly improved application properties, particularly with regard to their ability to stand up again. Alternatively, it is also possible to use bristles that are fastened in some other way, e.g. bristles that are tufted in a known way.

Figure 3:
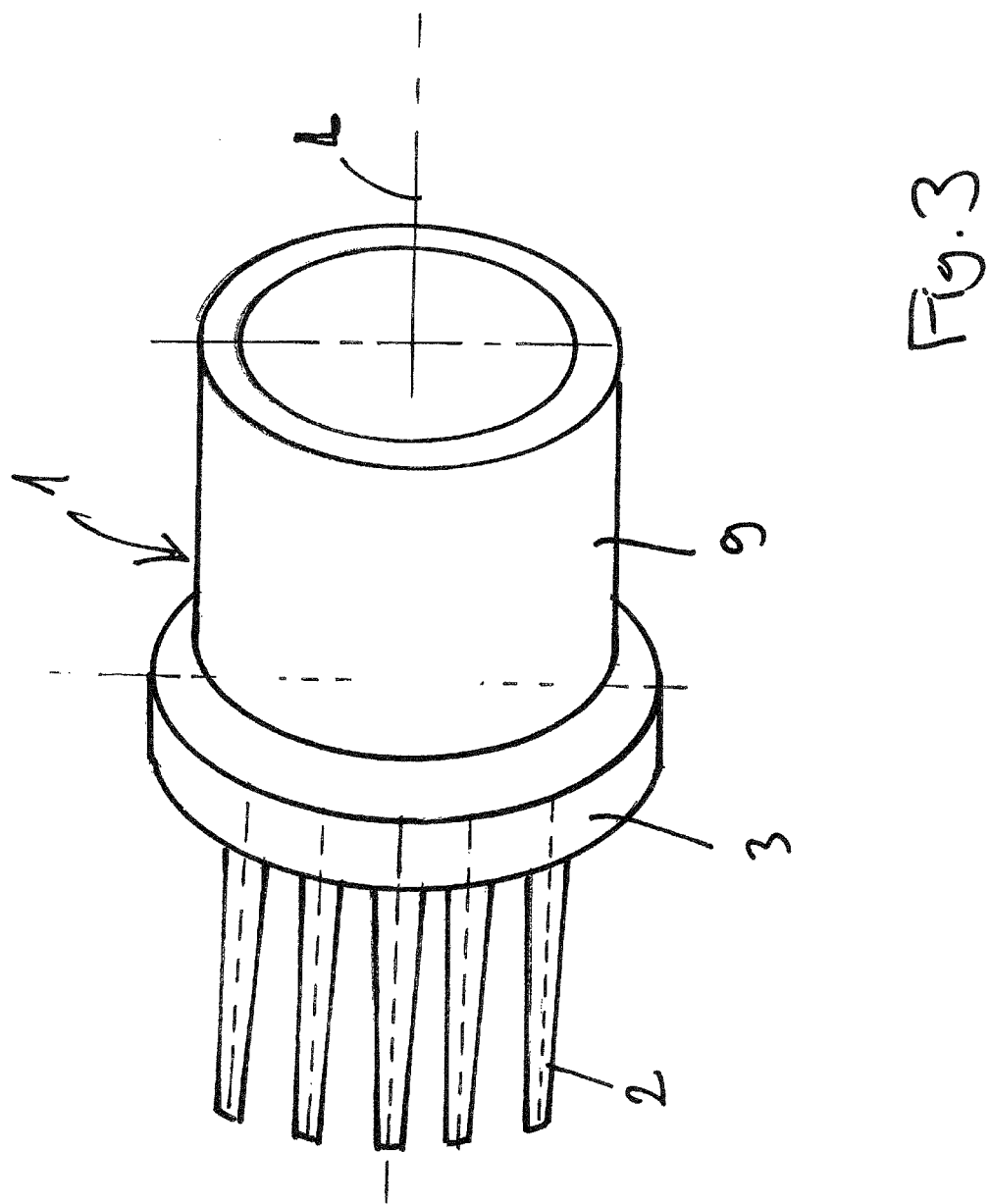
FIG. 3 shows a perspective view of the second exemplary embodiment.

FIG. 3 shows another exemplary embodiment for the finger support. This finger support is characterized by its round embodiment and by the fact that it transitions integrally into a tubular fitting 9. The drawing clearly shows the longitudinal axis L of the finger support. The drawing does not show the supply conduit 5 and also does not show the bristle conduit or conduits 4, which instead of or in addition to this, extend through at least one bristle and make it possible to dispense the substance, which is to be applied, via the bristles from one side of the finger support to the other. These devices are, however, also present in this exemplary embodiment.

The tubular fitting makes it significantly easier to insert the finger support into a tubular foil and attach it thereto with a reliable seal. To this end, the tubular foil is simply pulled or slid onto the tubular fitting like a stocking and then either welded to the tubular fitting, as shown in FIG. 4, or welded directly to the finger-supporting plate of the finger support, as explained above in conjunction with exemplary embodiment 1.

Figure 4:
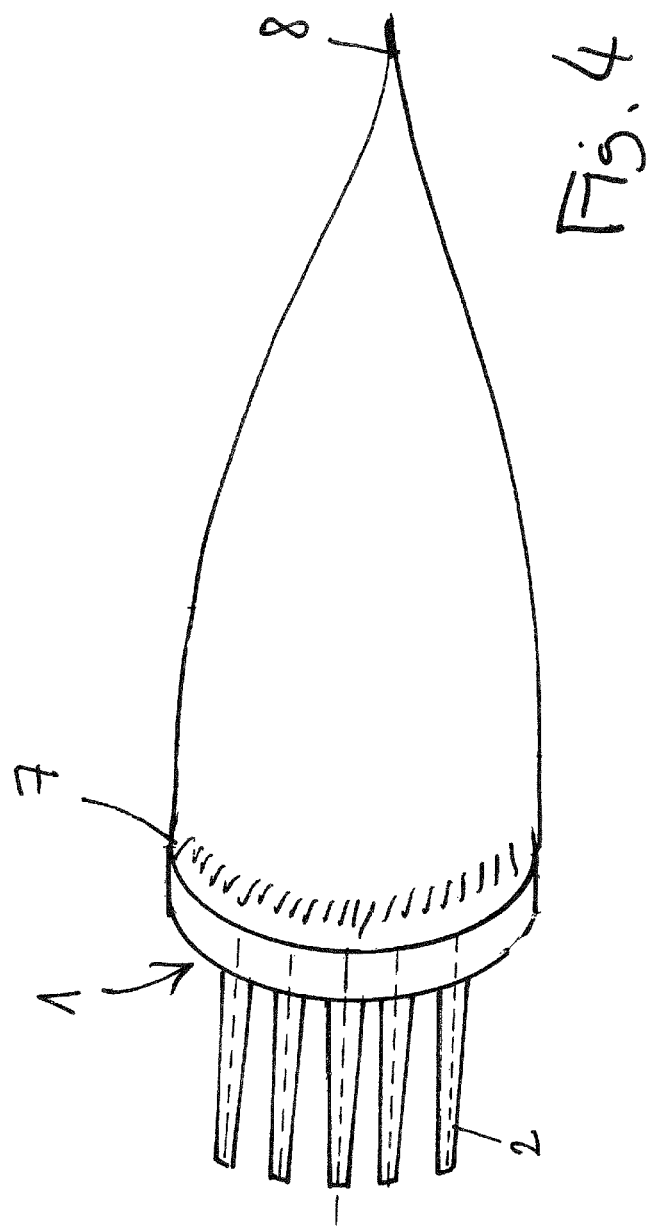
FIG. 4 shows a perspective view of the second exemplary embodiment in its complete form.

FIG. 4 shows the applicator that is produced in this way.

Figure 5:
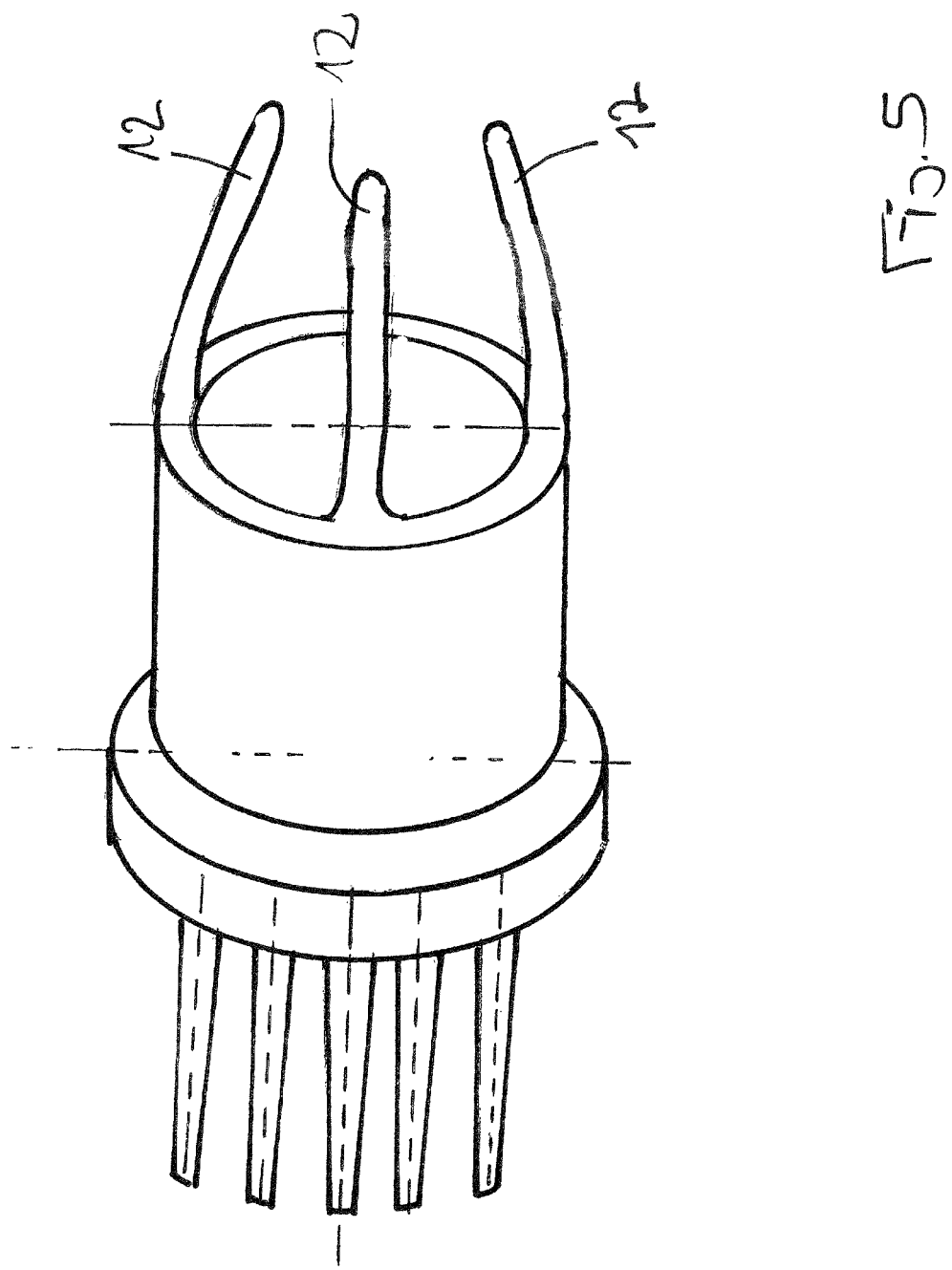
FIG. 5 shows a perspective view of a variant for implementing the second exemplary embodiment.

FIG. 5 shows one variant for implementing this exemplary embodiment; here, the tubular fitting transitions into a plurality of elastic spring arms 12 that preferably extend obliquely inward relative to the longitudinal axis L. These spreading arms 12 facilitate the insertion of the finger support into the tubular foil, because in this case, they function as guide runners that spread open the tubular foil. At the same time, these spreading arms 12 can also perform the function of keeping the tubular foil, which has been completely mounted and filled, in a spread-open position in an acceptable way. The function that is performed by these spreading arms depends on their length. The spreading arms are preferably an integral component of the tubular fitting; if no tubular fitting is provided, then they can be an integral component of the finger support and/or the finger-supporting plate.

Figure 6:
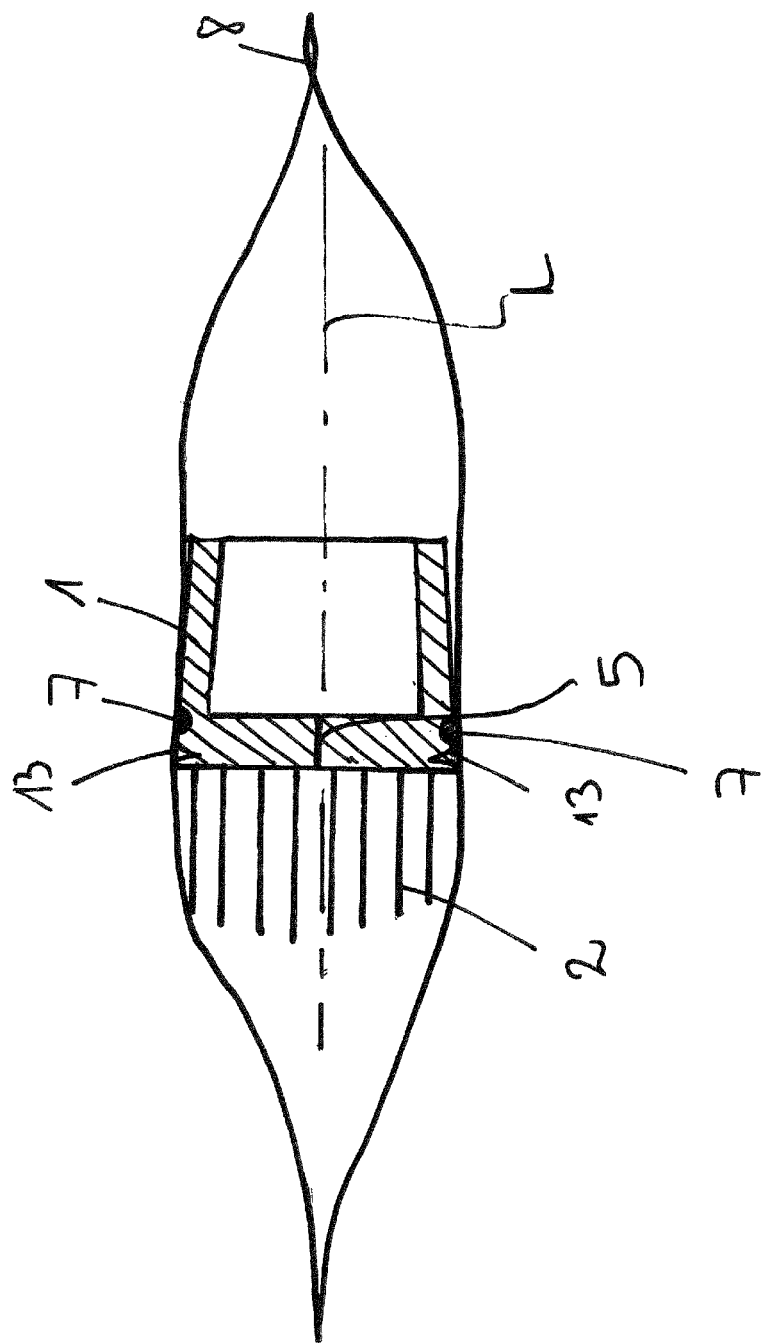
FIG. 6 shows another exemplary embodiment that is derived from the above-described exemplary embodiments.

FIG. 6 shows another exemplary embodiment that is derived from the above-described exemplary embodiment and is relatively closely related to the latter. Here, too, a preferably circular finger support is provided, which transitions integrally into a tubular fitting 9. As is relatively clear here, the tubular fitting 9 can be tapered in a slightly conical fashion in the direction of its end oriented away from the set of bristles in order to thus facilitate its insertion into the tubular foil. By contrast with the exemplary embodiment shown in FIG. 4, in the course of production, the finger support is slid so deep into the tubular foil that the tubular foil even protrudes past the fingers of the finger support. The tubular foil can then be welded closed at both ends and in this way, constitutes not only the reservoir for storing the substance to be applied, but also simultaneously constitutes a protection for the fingers, thus guaranteeing the hygienic state of the fingers until it is broken open. To this end, at corresponding locations, either in the vicinity of the finger support, as shown here, or adjacent to the finger support, the tubular foil can be provided with thin places, indentations, or similar expedients, which constitute a predetermined breaking point 13 at which the foil tears in order to free the set of fingers when one pulls on the end situated on the side with the set of fingers.

Figure 7:
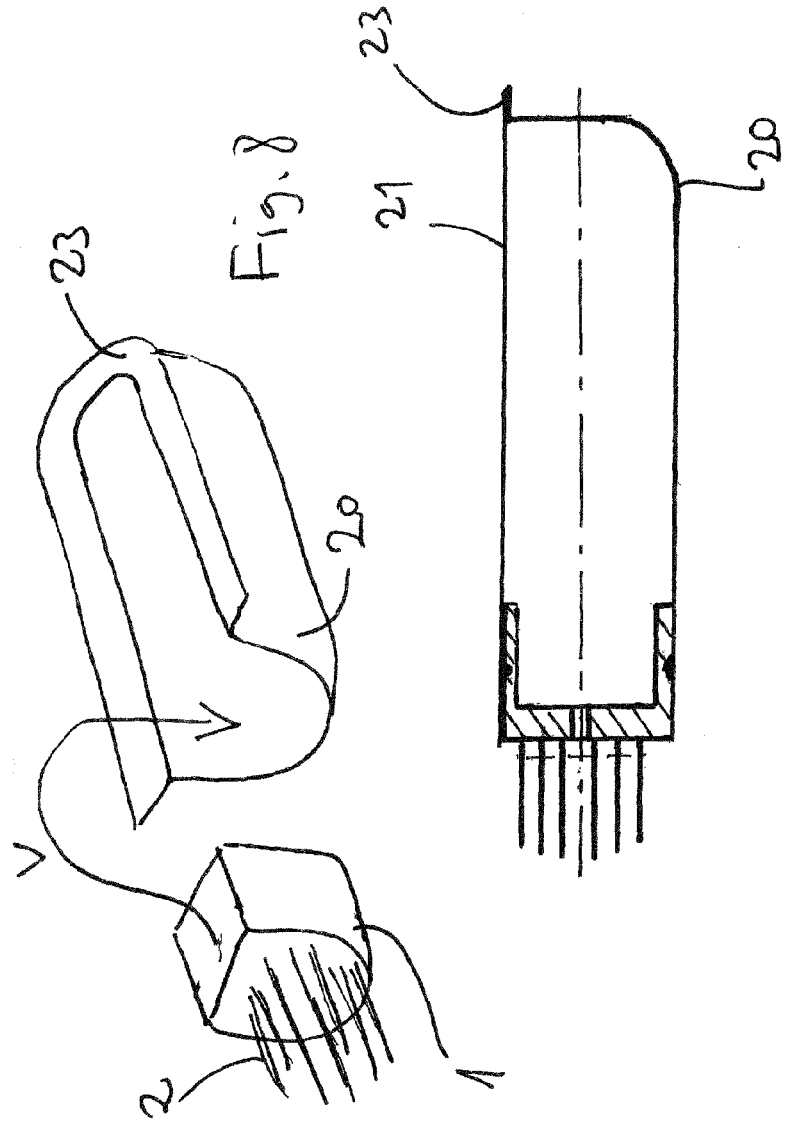
FIG. 7 shows a plan view of yet another exemplary embodiment.

FIG. 7 shows an entirely different exemplary embodiment of the invention. The finger support 1 according to the invention is used here as well. Preferably, the finger support 1 here has a tubular fitting 9 formed integrally onto it as well.

Figure 8:
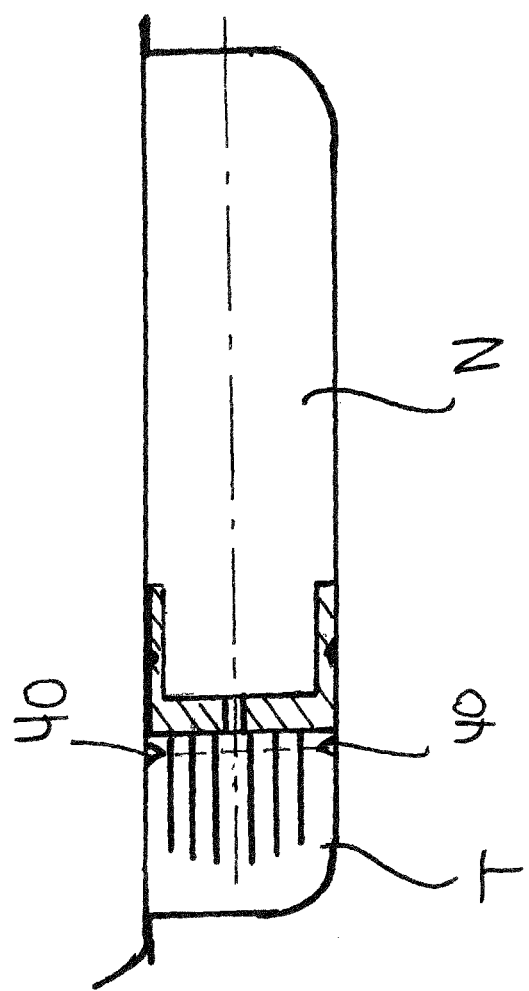
FIG. 8 shows a perspective view of the exemplary embodiment shown in FIG. 7.

The reservoir for the substance, which is to be applied, is embodied in an entirely different way in this exemplary embodiment. In this case, the reservoir is formed by a blister pack composed of a tray 20 and a foil 21 that seals the tray. The particular feature of the tray is that it is open at one end, as shown in FIG. 8. The finger support 1 is then inserted into this through a movement in the direction of the arrow V. Since the outer contour, i.e. the contour of the outer circumference of the finger support, corresponds to the cross-sectional profile of the tray 20, the finger support can be easily glued or welded to the tray 20. In this way, the tray then constitutes a trough that is completely closed except for its top, whose purpose is to contain the cosmetic that is to be applied. Since the top of the finger support is ideally embodied in the form of a surface that lies in a plane with the flange surfaces 23 of the tray after the finger support is attached, a foil can easily be sealed in place by welding or gluing it to the flange surfaces 23 of the tray and to the corresponding surface of the finger support.

FIG. 8.1 shows a modification of the above-mentioned exemplary embodiment. The difference in this exemplary embodiment, to which the above description of the preceding exemplary embodiment otherwise applies, is that in this case, the tray is embodied so that the finger support 1 divides it into a wet region N and a dry region T. The wet region, exactly as in the preceding exemplary embodiment, accommodates the cosmetic that is to be applied. The dry region provides a protection for the set of fingers, for example in order to keep it in a hygienically pristine condition until it is broken open. The tray 20 is sealed as a whole, even in the region of the set of fingers with the foil 21, which in this case as well, is welded to the flange surfaces 23 of the tray, but which in this case, extends all the way around.

Figure 9:
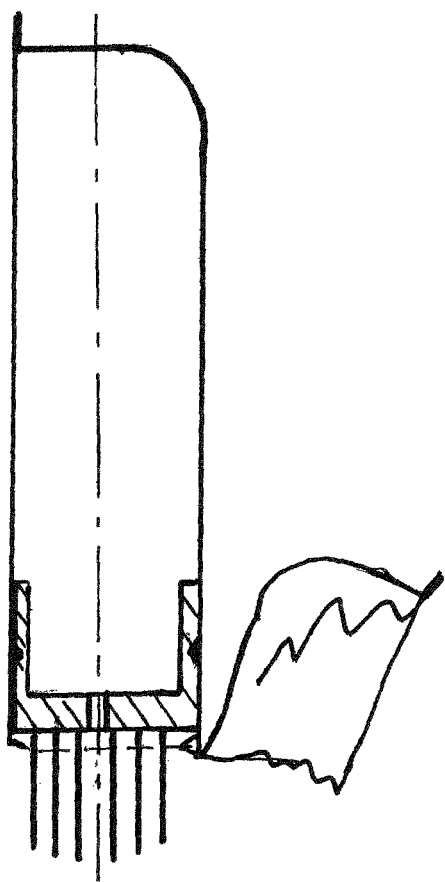
FIG. 9 shows a plan view of the exemplary embodiment illustrated in FIG. 8.1 in a position ready for application.

Preferably, the tray has a predetermined breaking point, for example in the form of one or more indentations 40 shown in FIG. 8.1. This embodiment makes it possible to break the section of the tray that protects the set of fingers apart from the rest of the tray, which serves to hold the cosmetic to be applied and to fold it aside far enough that the application can be carried out as shown in FIG. 9. Ideally, such a folding is not used and instead, the section of the tray to be moved out of the way is embodied so it can be removed completely.

Protection is also claimed for a method for producing the above-described applicators and applicator units.

The invention claimed is:

1. An internally supplied applicator for applying a fluid substance, in particular a cosmetic or pharmaceutical product, comprising:
a solid finger support with a plurality of injection molded fingers and at least one supply conduit for conveying the substance from a side of the finger support oriented away from the fingers to a side of the finger support that is equipped with the fingers; wherein the side of the finger support oriented away from the fingers is adjoined by a crushable foil packet that contains a reservoir of the substance that is to be applied so that pressing on the foil packet causes a volume of the substance, which is to be applied, to be dispensed through the supply conduit.

2. The internally supplied applicator according to claim 1, wherein the linger support is intrinsically rigid.

3. The internally supplied applicator according to claim 1, wherein the foil packet is welded only to a circumference surface of the finger support.

4. The internally supplied applicator according to claim 1, wherein the foil packet is a tubular foil that is extruded or blown so that it is seamless around its outer circumference direction and has a all thickness of at most 0.5 mm.

5. The internally supplied applicator according to claim 4, wherein the tubular foil is intrinsically welded at an end oriented away from the finger support.

6. The internally supplied applicator according to claim 4, wherein the finger support is composed of a finger-supporting plate, which on its side oriented away from the fingers, transitions integrally into a tubular fitting that the tubular foil encompasses like a stocking.

7. The internally supplied applicator according to claim 6, wherein the foil packet or the tubular foil is welded to the outer circumference of the tubular fitting.

8. The internally supplied applicator according to claim 6, wherein the tubular fitting tapers toward its end oriented away from the finger support and is embodied in a conical shape.

9. The internally supplied applicator according to claim 6, wherein the finger support or its tubular fitting transitions into at least two spreading arms.

10. The internally supplied applicator according to claim 4, wherein the foil packet or the tubular foil is welded to the outer circumference of the finger-supporting plate.

11. The internally supplied applicator according to claim 1, wherein the bristle support is embodied in the shape of a boat.

12. The internally supplied applicator according to claim 1, wherein the finger support has a thread for screwing on a screw cap or has a snap element for snapping on a cap.

13. The internally supplied applicator according to claim 4, wherein the tubular foil also encompasses the finger support at its finger end and is intrinsically welded to its end there.

14. An applicator unit composed of at least one applicator according to claim 1, wherein the applicator is inserted into a blister pack, which is composed of a tray that has a recess that accommodates the applicator and at least the recess that accommodates the applicator is sealed on one side with a foil.

15. An internally supplied applicator for applying a fluid substance, in particular a cosmetic or pharmaceutical product, comprising:
a static finger support with a plurality of fingers injection molded onto the static finger support and at least one supply conduit for conveying the substance from a side of the finger support oriented away from the fingers to a side of the finger support that is equipped with the fingers; wherein the side of the finger support oriented away from the fingers is adjoined by a crushable blister pack, which is composed of a tray and a foil that seals the tray, and which contains a reservoir of the substance that is to be applied; and wherein pressing on the tray and/or the foil that seals the tray causes a volume of the substance, which is to be applied, to be dispensed through the supply conduit.

16. The internally supplied applicator according to claim 15, wherein the tray and the foil that seals the tray are welded to the finger support.

17. The internally supplied applicator according to claim 15, wherein the finger support divides the tray into a dry region and a wet region, and the dry region accommodates the plurality of fingers of the finger support; the tray has a predetermined breaking point in the dry region, which makes it possible, before use, to break off a part of the tray that protects the plurality of fingers until the use, and to completely remove the part of the tray or move the part of the tray out of the way so that the application can be carried out with the aid of the plurality of fingers.

18. The internally supplied applicator according to claim 15, wherein the finger support divides the tray into a dry region and a wet region and the dry region accommodates the plurality of fingers of the finger support; and in the dry region, the tray is sufficiently thin-walled so that the tray can be laterally folded over so that the application can be carried out with the aid of the plurality of fingers.

19. A method for producing the applicator of claim 1, comprising:
blowing, extruding, or welding a tubular foil;
at least partially sliding a finger support that is equipped with a plurality of injection molded fingers into the tubular foil and then welded the finger support to the tubular foil;
subsequently filling the tubular foil with a fluid substance, in particular a cosmetic or pharmaceutical product substance, to be applied; and then welding the tubular foil completely closed.

20. The method according to claim 19, comprising inserting the finger support into a beginning of the tubular foil and welding the finger support to the tubular foil before an entire length of the tubular foil that is required for this applicator is blown and/or extruded.

21. The method according to claim 19, comprising dispensing the substance to be applied into the tubular foil while the latter is still at a temperature of at least 60°.

\* \* \* \* \*